(12) United States Patent
Kim

(10) Patent No.: US 9,993,201 B2
(45) Date of Patent: Jun. 12, 2018

(54) WEARABLE DEVICE

(71) Applicant: SAMSUNG ELECTRONICS CO., LTD., Suwon-si (KR)

(72) Inventor: Sang kyu Kim, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 489 days.

(21) Appl. No.: 14/822,968

(22) Filed: Aug. 11, 2015

(65) Prior Publication Data
US 2016/0310074 A1   Oct. 27, 2016

(30) Foreign Application Priority Data

Apr. 22, 2015 (KR) .................. 10-2015-0056655

(51) Int. Cl.
| | | |
|---|---|---|
| *A61B 5/1455* | (2006.01) | |
| *A61B 5/00* | (2006.01) | |
| A61B 90/30 | (2016.01) | |
| A61B 5/145 | (2006.01) | |

(52) U.S. Cl.
CPC ............ *A61B 5/681* (2013.01); *A61B 5/0075* (2013.01); *A61B 5/1455* (2013.01); *A61B 5/14532* (2013.01); *A61B 2090/306* (2016.02); *A61B 2562/0233* (2013.01); *A61B 2562/0238* (2013.01)

(58) Field of Classification Search
CPC ... A61B 5/1455; A61B 5/14532; A61B 5/681; A61B 5/0075; A61B 5/0079; A61B 2562/0233; A61B 2562/0238
See application file for complete search history.

(56) References Cited

U.S. PATENT DOCUMENTS

| 5,825,488 A | * | 10/1998 | Kohl | ...................... G01N 21/49 |
|---|---|---|---|---|
| | | | | 600/310 |
| 7,299,080 B2 | * | 11/2007 | Acosta | .................. A61B 5/1455 |
| | | | | 800/310 |
| 2005/0054907 A1 | | 3/2005 | Page et al. | |
| 2006/0253010 A1 | * | 11/2006 | Brady | ................ A61B 5/14552 |
| | | | | 600/324 |
| 2008/0004510 A1 | * | 1/2008 | Tanzawa | ................ A61B 5/742 |
| | | | | 600/301 |
| 2014/0128691 A1 | | 5/2014 | Olivier | |
| 2014/0200423 A1 | * | 7/2014 | Eisen | .................. A61B 5/14551 |
| | | | | 600/340 |

(Continued)

FOREIGN PATENT DOCUMENTS

JP          2014-10046 A     1/2014

*Primary Examiner* — Eric Winakur
(74) *Attorney, Agent, or Firm* — Sughrue Mion, PLLC

(57) ABSTRACT

A wearable device includes a main body, and a strap connected to the main body, the strap being configured to be flexible. The wearable device further includes a light source disposed in the strap, the light source being configured to emit light onto a surface of a user. The wearable device further includes a spectrum portion disposed in the main body, and an optical waveguide disposed in the strap, the optical waveguide being configured to receive the emitted light traveling into and out from the surface, and transmit the received light to the spectrum portion. The wearable device further includes a detector disposed in the main body, the detector being configured to detect the transmitted light dispersing through the spectrum portion.

17 Claims, 8 Drawing Sheets

(56) References Cited

U.S. PATENT DOCUMENTS

2014/0332675 A1 11/2014 Fujita et al.
2014/0339428 A1 11/2014 O'Brien et al.
2015/0157261 A1 6/2015 Sakagami

* cited by examiner

WEARABLE DEVICE

CROSS-REFERENCE TO RELATED APPLICATION

This application claims priority from Korean Patent Application No. 10-2015-0056655, filed on Apr. 22, 2015, in the Korean Intellectual Property Office, the disclosure of which is incorporated herein by reference in its entirety.

BACKGROUND

1. Field

Apparatuses consistent with exemplary embodiments relate to a wearable device.

2. Description of the Related Art

Wearable devices have come to gain much attention as new prospects of the next-generation smart device market. Like a pair of glasses, a watch, or clothes, such wearable devices can be worn on the human body, and yet they are electronic devices. Wearable devices have various sensors installed therein that enable them to measure the wearer's heart rate, amount of exercise, sleep pattern, etc.

Because spectrometers are used in performing qualitative analysis, quantitative analysis, state analysis of a target by measuring the spectrum that the target emits or absorbs, they may thus be applied to the task of non-invasively measuring the biosignals of a living human body, such as blood sugar and cholesterol levels. So if a spectrometer were to be installed in a wearable device, it would mean that various biosignals could be non-invasively measured to be used in the field of mobile healthcare.

However, if a spectrometer is to be installed in a wearable device that is to be worn, for example, on a user's wrist, the spectrometer would have to be small, which may cause a decline in performance. Therefore, a technology that allows for a spectrometer, which has been installed in a wearable device, to function without a decline in performance may be used.

SUMMARY

Exemplary embodiments address at least the above problems and/or disadvantages and other disadvantages not described above. Also, the exemplary embodiments are not required to overcome the disadvantages described above, and may not overcome any of the problems described above.

According to an aspect of an exemplary embodiment, there is provided a wearable device including a main body, and a strap connected to the main body, the strap being configured to be flexible. The wearable device further includes a light source disposed in the strap, the light source being configured to emit light onto a surface of a user. The wearable device further includes a spectrum portion disposed in the main body, and an optical waveguide disposed in the strap, the optical waveguide being configured to receive the emitted light traveling into and out from the surface, and transmit the received light to the spectrum portion. The wearable device further includes a detector disposed in the main body, the detector being configured to detect the transmitted light dispersing through the spectrum portion.

The spectrum portion may include a linear variable filter.

The spectrum portion may include a light-transmissive member configured to enable the transmitted light to pass therethrough, and a reflective mirror disposed on an outer surface of the light-transmissive member, the reflective mirror being configured to reflect the passed-through light.

The spectrum portion may further include a diffraction grating disposed on the outer surface of the light-transmissive member, the diffraction grating being configured to disperse the reflected light, and transmit the dispersed light to the detector.

The optical waveguide may be an optical fiber.

The wearable device may further include a light-collecting member disposed in the strap, the light-collecting member being configured to collect the emitted light traveling into and out from the surface, and transmit the collected light to the optical waveguide.

The light source may be configured to emit the light having a wavelength of a near-infrared frequency, and the detector may be configured to detect the dispersed light having the wavelength of the near-infrared frequency.

The strap may include a first strap member including the optical waveguide therein, the first strap member extending from a first end of the main body. The strap may further include a second strap member extending from a second end of the main body, and a buckle including the light source therein, the buckle being connected to an end of the first strap member, and the buckle being configured to fasten and unfasten the second strap member to and from first strap member.

The buckle may include an accommodation groove disposed to face the surface, the accommodation groove being configured to house the light source, and the accommodation groove being inserted a light incident end of the optical waveguide therein. The buckle may further include a window configured to enable the emitted light to pass therethrough, and cover the accommodation groove.

The second strap member may include a battery therein.

The strap may include a first strap member including the light source and the optical waveguide therein, the first strap member extending from a first end of the main body. The strap may further include a second strap member extending from a second end of the main body.

The wearable device may further include a processor disposed in the main body, the processor being configured to operate the light source, and process a signal that is received from the detector. The wearable device may further include a battery configured to provide power to the processor.

The wearable device may further include an operator configured to relay a command of the user to the processor.

The battery may be configured to be flexible, and the battery may be disposed in the strap.

The wearable device may further include a wireless communicator disposed in the main body, the wireless communication being configured to transmit the processed signal.

The wearable device may further include a display disposed in the main body, the display being configured to display information of the processed signal.

The surface of the user may be skin of the user.

BRIEF DESCRIPTION OF THE DRAWINGS

The above and/or other aspects will be more apparent by describing exemplary embodiments with reference to the accompanying drawings in which.

DETAILED DESCRIPTION OF THE EXEMPLARY EMBODIMENTS

Figure 1:
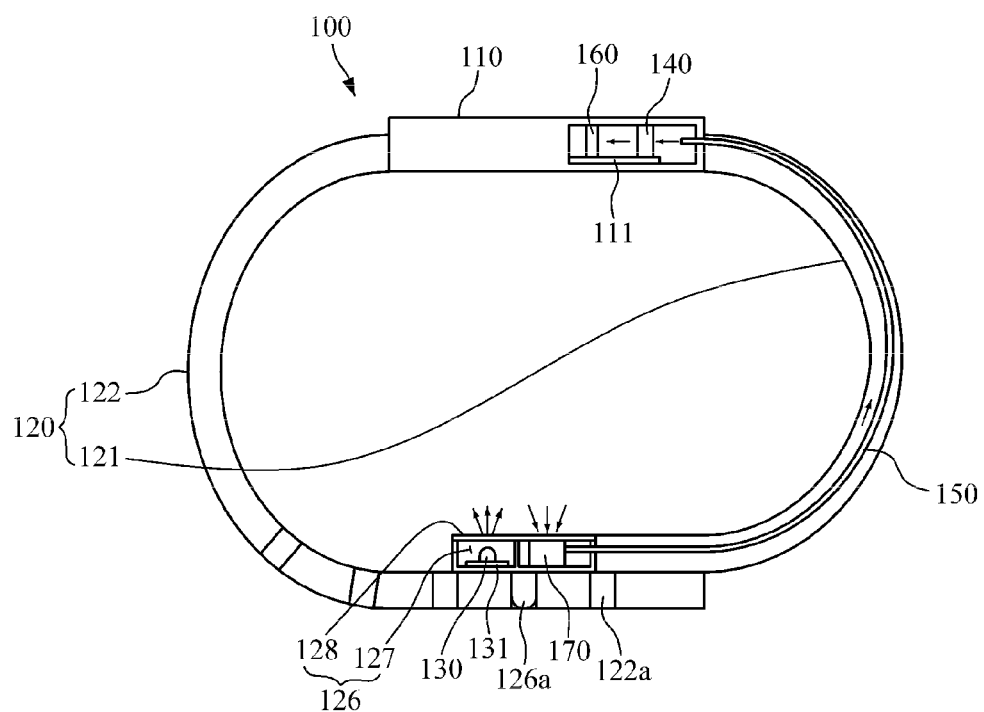
FIG. 1 is a diagram illustrating a wearable device according to an exemplary embodiment.

Exemplary embodiments are described in greater detail herein with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail because they would obscure the description with unnecessary detail.

Figure 2:
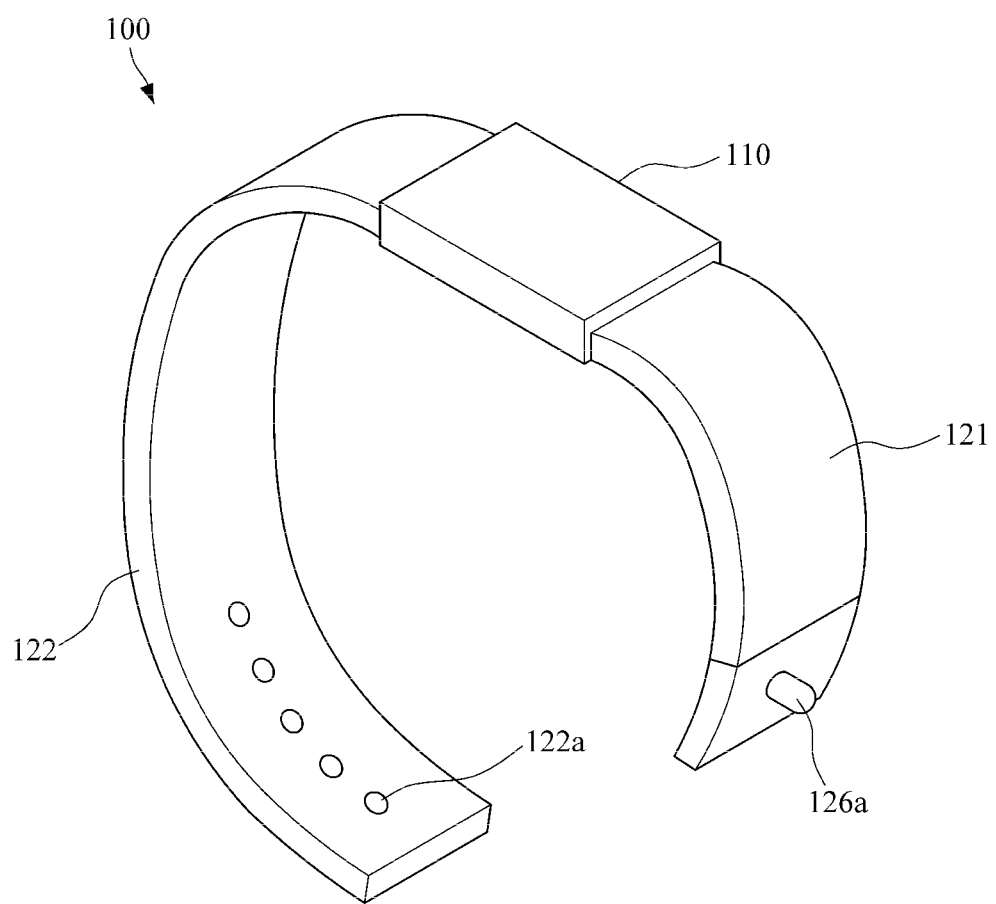
FIG. 2 is a perspective view illustrating the wearable device of FIG. 1.

FIG. 1 is a diagram illustrating a wearable device 100 according to an exemplary embodiment. FIG. 2 is a perspective view illustrating the wearable device 100 of FIG. 1.

Referring to FIGS. 1 and 2, the wearable device 100 includes a main body 110, a strap 120, a light source 130, a spectrum portion 140, an optical waveguide 150, and a detector 160.

The main body 110 includes the spectrum portion 140 and the detector 160 therein. The strap 120 is connected to the main body 110. The strap 120 is flexible and is thus capable of bending to wrap around or unwrap from a user's wrist, allowing the user to easily wear the main body 110 on his or her wrist or remove it. In such a manner, the strap 120 may be made in a manner that enables the user to wear the main body 110 on his or her wrist.

The light source 130 is built into the strap 120. The light source 130 emits light onto a user's skin. The spectrum portion 140 is built into the main body 110. The light that has emitted from the light source 130 travels into and back from the skin, and is then dispersed by the spectrum portion 140. That is, the light is emitted from the light source 130 onto the user's skin and travels under the skin to the biological tissues, and this light returns after having reacted to the biological tissues. The light that has returned is then received by the spectrum portion 140, which disperses this light into a spectrum and then relays the spectrum onto the detector 160.

The optical waveguide 150 is built into the strap 120. The optical waveguide 150 receives the light that has been emitted from the light source 130 and has travelled into and back from the user's skin, and then transmits the light to the spectrum portion 140. The detector 160 is built into the main body 110. The detector 160 detects the light that is dispersed through the spectrum portion 140. The light detected by the detector 160 may be used to measure biosignals, such as blood sugar and cholesterol levels, whereby the spectroscopy used may be infrared spectroscopy, Raman spectroscopy, etc.

The light source 130, the spectrum portion 140, the optical waveguide 150, and the detector 160, which are included in the above-mentioned wearable device 100, configure a spectrometer. These components of the spectrometer 140 are scattered and situated throughout the device 100 (i.e., the spectrum portion 140 and the detector 160 are housed by the main body 110 of the device, while the light source 130 and optical waveguide 150 are built into the strap 120), and in effect, the spectrometer is allowed to be small and thus have a suitable size for the wearable device 100.

In addition, although the spectrometer is small, there is still sufficient area for the light to be received, wherein the light is emitted from the light source 130 and returns, because the light source 130 and the optical waveguide 150 are built in along a portion of the strap 120. Thus, the spectrometer may be installed in the wearable device 100 and function without any decline in performance, making it possible for the wearable device 100 to non-invasively measure a variety of biosignals.

Because the light source 130 and the detector 160 are scattered and situated, respectively, in the strap 120 and in the main body 110, the distance between the light source 130 and the detector 160 becomes the farthest it can be. Such distance minimizes disturbance caused by thermal noise, which is made from the heat generated when the light source 130 operates from being placed on the detector 160.

The wearable device 100 includes a light-collecting member 170, which is built into the strap 120 to collect the light that travels into and back from a user's skin. The light-collecting member 170 then transmits the collected light to the optical waveguide 150. To collect light, the light-collecting member 170 may include lenses, etc. In such a case, the light-collecting member 170 is built on the strap 120 so that there is sufficient area for collecting light. The light-collecting member 170 may be omitted.

The light source 130 may emit light that has a wavelength of a near-infrared frequency. In this case, the detector 160 may be configured to detect the near-infrared light. A near-infrared ray can be defined as one that is between 1000 nm and 2200 nm. The light source 130 may be a halogen lamp or the like and is mounted on a circuit board 131 that is built into the strap 120. The detector 160 may be an indium gallium arsenide (InGaAs) photodiode or the like and is mounted on a circuit board 111 that is built into the main body 110.

The optical waveguide 150 may be optical fiber. The optical fiber has a core, which is surrounded by cladding that has a lower refractive index than the core. Light travelling in through the optical fiber is guided along the fiber core by total internal reflection. Because optical fiber is flexible, it can freely bend with the strap 120. One end of the optical fiber is placed to receive the light that returns after being emitted from the light source 130, and the other end is placed inside the main body 110 so that light may be transferred to the spectrum portion 140.

The strap 120 includes two members: one which will hereinafter be referred to as a first strap member 121 and the other as a second strap member 122. The first strap member 121 includes the optical waveguide 150 therein, and extends from one end of the main body 110. The first strap member 121 has an inner cavity that is formed longitudinally, into which an optical fiber can be inserted through one opening end. In another example, the first strap member 121 may include two pieces that are coupled, with the optical fiber placed in between. The first strap member 121 may be made of urethane, silicon, rubber, leather, etc.

The second strap member 122 extends from the other end of the main body 110. The second strap member 122 may be made so that it is long enough to overlap the first strap member 121, and thus the first strap member 121 and the second strap member 122 wrap around a user's wrist. The second strap member 122 may be made of the same material as the first strap member 121.

A buckle 126 is connected to the extending end of the first strap member 121 so that the second strap member 121 may be fastened to or unfastened from the first strap member 121. The buckle 126 includes a locking protrusion 126a that protrudes out from the buckle's surface that has no contact with a user's wrist.

The second strap member 122 includes a plurality of locking holes 122a, longitudinally arranged thereon along the extending end, and into which the locking protrusion 126a is selectively inserted so that the second strap member 122 covers the buckle 126. Therefore, the user can fasten the strap members (i.e. insert the locking protrusion 126a into one of the locking holes 122a) at a length of his or her choice based on the user's wrist size.

The buckle 126 includes the light source 130 therein. In such a case, the buckle 126 includes an accommodation groove 127 and a window 128. The accommodation groove 127, which is formed to face a user's skin, houses the light source 130 and includes a light incident end of the optical waveguide 150 that is inserted therein. The buckle 126 may include electrical insulators such as plastic to inhibit unwanted electric charges. The accommodation groove 126 may be partitioned to house the light source 130 and the optical waveguide 150 separately to prevent the light emitting from the light source 130 from directly flowing into the optical waveguide 150. In the accommodation groove 126, the light-collecting member 170 may be placed in a manner so that it corresponds to the light incident end of the optical waveguide 150.

The window 128 has a property of enabling a light to pass therethrough and covers the accommodation groove 127. The light emitted from the light source 130 is transmitted through the window 128 so that the light may enter into a user's skin, and the light that travels back after having passed through the user's skin is transmitted back through the window 128 so that the light may enter into the optical waveguide 150. The window 128 may be made of sapphire glass. The gap between the window 128 and the accommodation groove 127 may be sealed off.

When the light source 130 and the optical waveguide 150 are built into the buckle 126 and the buckle 126 is placed on the strap's surface that is in contact with a user's inner wrist, biosignals are easily measured via the inner wrist, which is an area where the skin is thinner. The aforementioned characteristics of the buckle 126 allow for space in the wearable device 100 to be used efficiently.

Figure 3:
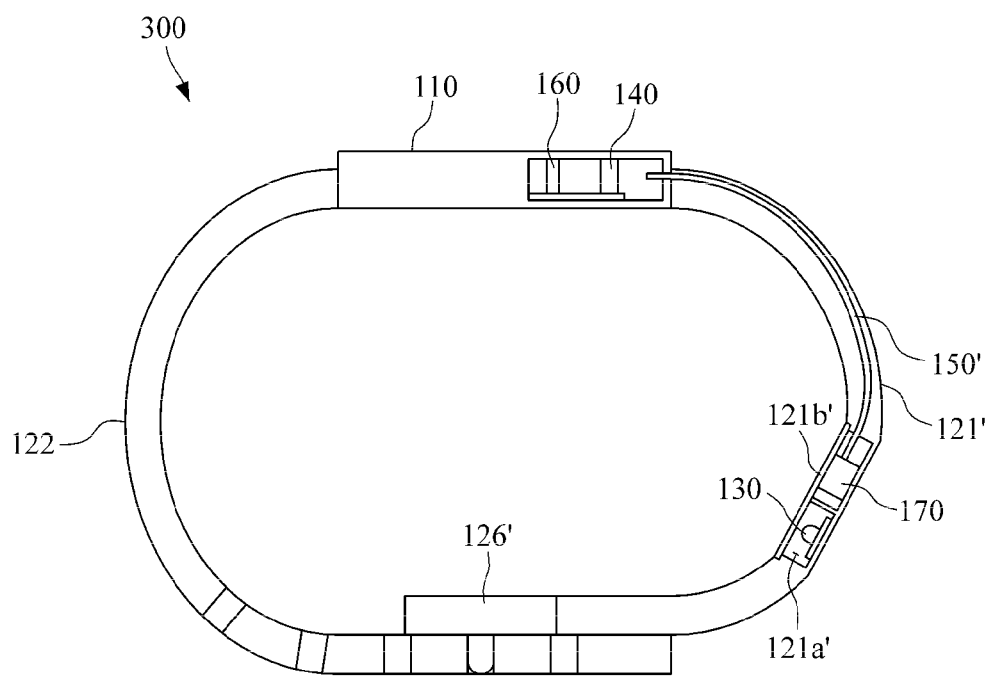
FIG. 3 is a diagram illustrating a wearable device in which both a light source and an optical waveguide are changed, according to another exemplary embodiment.

FIG. 3 is a diagram illustrating a wearable device 300 in which both the light source 130 and the optical waveguide 150 are changed, according to another exemplary embodiment.

As illustrated in FIG. 3, the light source 130 is not built into a buckle 126' but into a first strap member 121'. The first strap member 121' includes an accommodation groove 121a' as the aforementioned buckle 126 does as illustrated in FIG. 1. The accommodation groove 121a', which is formed to face a user's skin, houses the light source 130 and includes the light incident end of an optical waveguide 150' that is inserted therein. The accommodation groove 121a' is covered by a window 121b' that can transmit light.

Referring to FIGS. 1 to 3, the buckles 126 and 126' may be omitted, and instead, the strap members A and B can be made to stay wrapped around a user's wrist using elasticity. Also, one or more other fastening materials, such as Velcro®, may be used instead of the buckles 126 and 126'. Furthermore, the second strap member 122 may be omitted, and instead, the first strap member may be made to extend longer so that the extending end may be fastened to the main body or unfastened. In another variation, the main body may be installed where the strap members A and B connect to each other.

Figure 4:
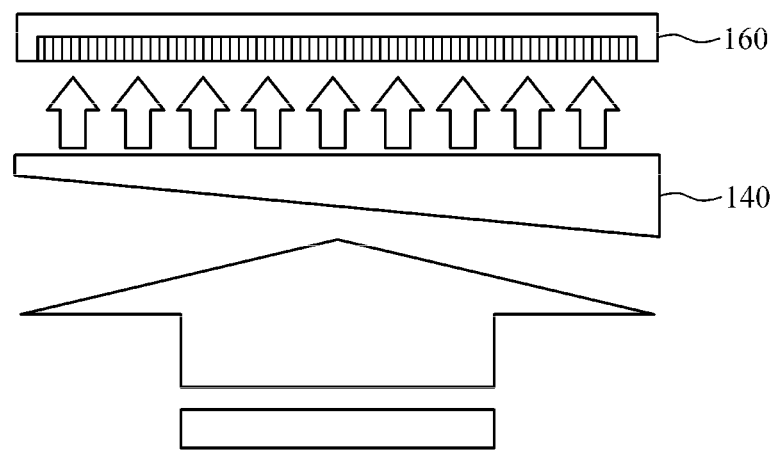
FIG. 4 is a diagram illustrating a spectrum portion and a detector in FIG. 1.

FIG. 4 is a diagram illustrating the spectrum portion 140 and the detector 160 in FIG. 1.

As illustrated in FIG. 4, the spectrum portion 140 includes a linear variable filter (LVF). An LVF has spectral properties that vary linearly from one end of a length to the other entirely. Thus, the LVF can disperse an incident ray into a spectrum according to the order of wavelengths. Though an LVF is compact in size, it has powerful spectral capability.

The detector 160 includes photodiode arrays, which include multiple photodiodes in an arrangement. The photodiode arrays are placed in a manner so that they may detect the light that is dispersed through the LVF.

Figure 5:
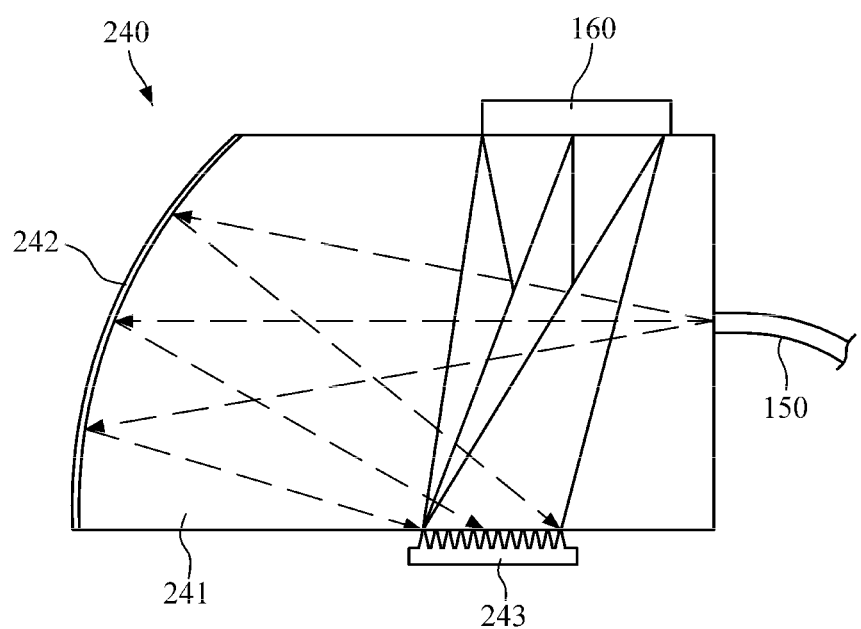
FIG. 5 is a top plan view illustrating a spectrum portion according to another exemplary embodiment.
Figure 6:
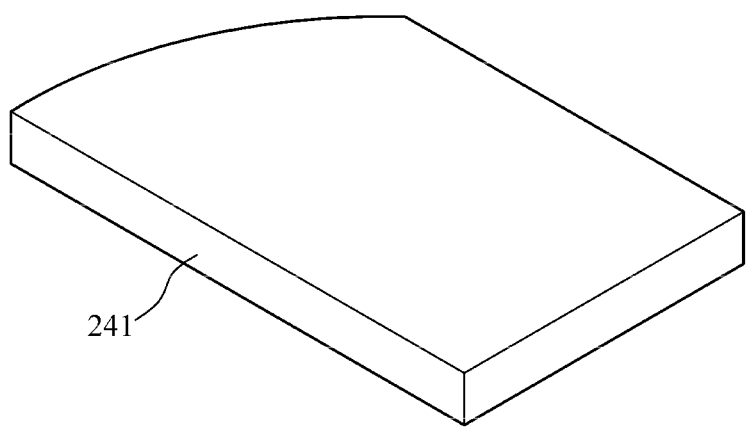
FIG. 6 is a perspective view illustrating a light-transmissive member of FIG. 5.

FIG. 5 is a top plan view illustrating a spectrum portion 240 according to another exemplary embodiment. FIG. 6 is a perspective view illustrating a light-transmissive member 241 of FIG. 5.

As illustrated in FIGS. 5 and 6, the spectrum portion 240 includes the light-transmissive member 241, a reflective mirror 242, and a diffraction grating 243. The light transmitted from the optical waveguide 150, e.g., the optical fiber, passes through the light-transmissive member 241. The reflective mirror 242 is placed on the outer surface of the light-transmissive member 241 so that it may reflect the light that has passed through the light-transmissive member 241.

The diffraction grating 243 is placed on the outer surface of the light-transmissive member 241 to disperse the light that is reflected by the reflective mirror 242 and then to transmit the dispersed light to the detector 160. The diffraction grating 243 includes a plurality of grooves on a plane or on a concave surface, and is formed so that it may create a spectrum through interference among the lights that have been diffracted at each of the grooves.

The light-transmissive member 241 may be formed to take the shape of what looks like a rectangular plane that is of uniform thickness, one end of which is cut to form a curved surface. The reflective mirror 242 is formed on the curved surface of the light-transmissive member 241. Light from the optical fiber enters the rectangular end of the light-transmissive member 241 and then passes through to the other end, the end with the curved surface.

Also, the light-transmissive member 241 has two parallel surfaces, in which one surface is longer than the other and each of which is connected to the curved surface. Among the two surfaces, the detector 160 is placed on the shorter surface while the diffraction grating 243 is placed on the longer surface. The detector 160 may include photodiode arrays. The inner walls of the main body 110 may hide the light-transmissive member 241, excluding the parts where the optical fiber, the diffraction grating 243, and the detector 160 are placed. Thus, no light is leaked.

Figure 7:
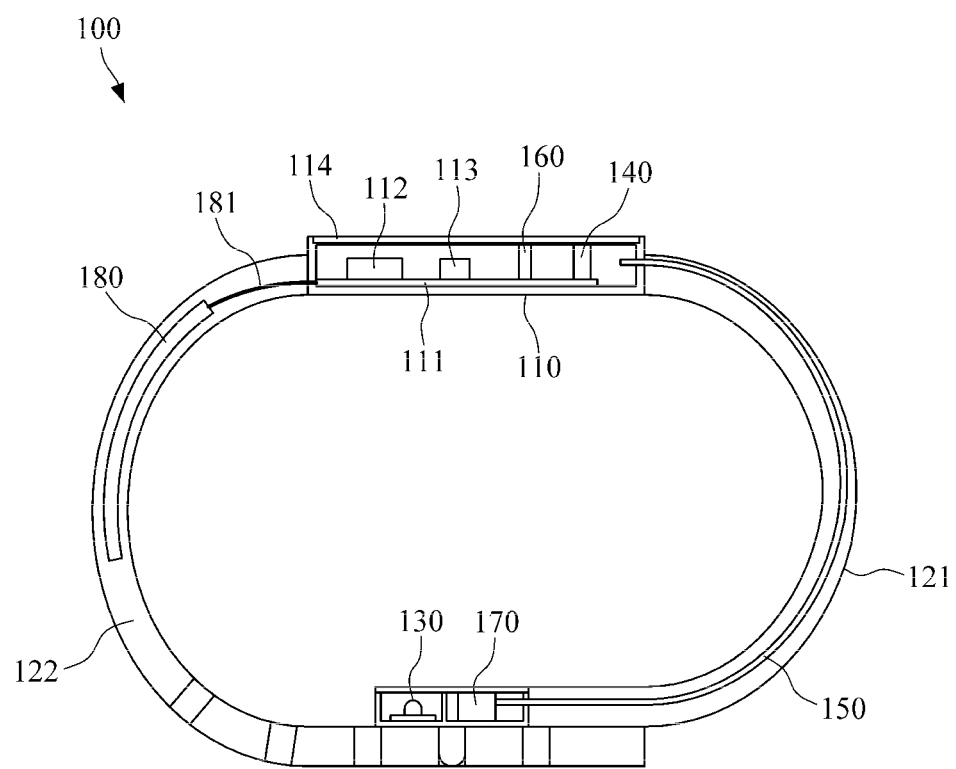
FIG. 7 is a diagram illustrating a main body and a battery of the wearable device of FIG. 1.
Figure 8:
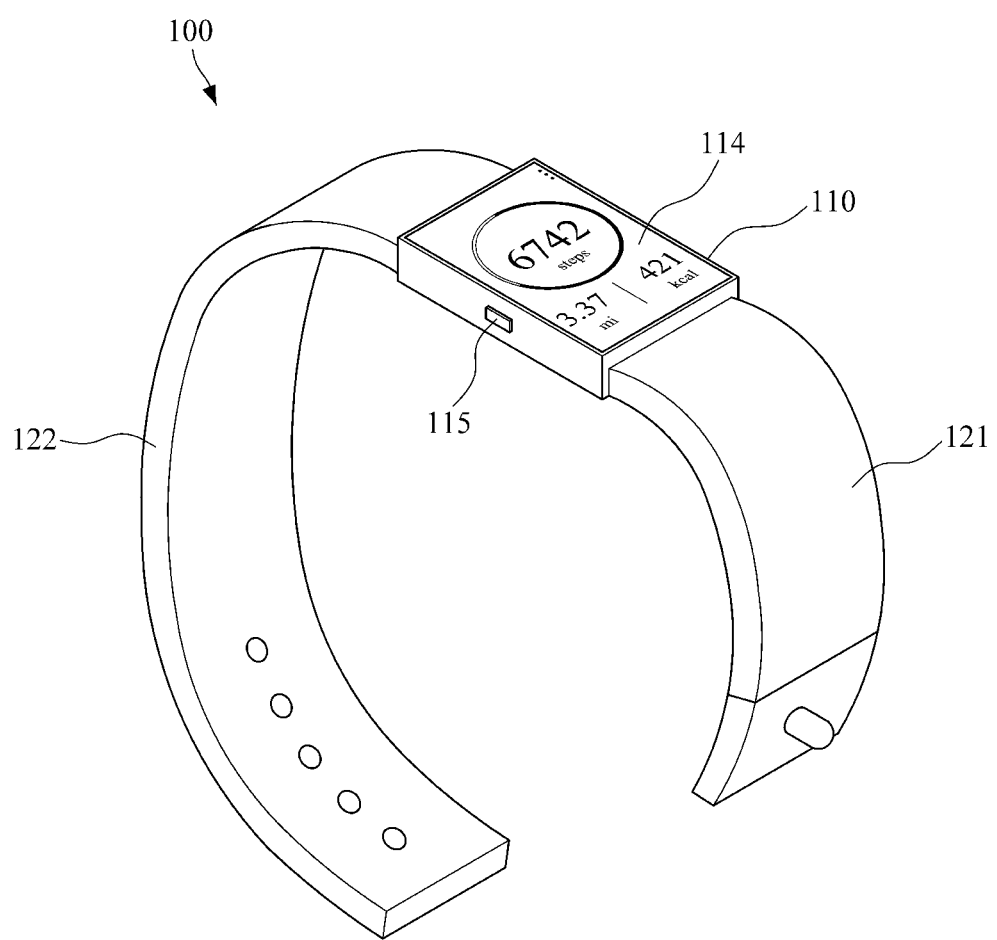
FIG. 8 is a perspective view illustrating the main body of FIG. 7.

FIG. 7 is a diagram illustrating the main body 110 and a battery 180 of the wearable device 100 of FIG. 1. FIG. 8 is a perspective view of the main body 110 of FIG. 7.

Referring to FIGS. 7 and 8, a processor 112 is built into the inner cavity of the main body 110. The processor 112 is housed in the inner cavity of the main body 110 along with the spectrum portion 140 and the detector 160, and the processor 112 and the detector 160 are mounted onto the circuit board 111 therein so that the processor 112 is electrically connected to the detector 160. The processor 112 operates the light source 130.

The processor 112 processes a signal that is input from the detector 160, thereby converting the signal to a biosignal which a user can understand. The light source 130 may be connected to the processor 112 by an electrical wire that is placed inside the strap 120, or inside the first strap member 121.

In a case in which the wearable device 100 is equipped with sensors to measure a heart rate, amount of exercise, sleep pattern, etc., the processor 112 may process all types of signals that are input from the sensors, thereby converting the heart rate, the amount of exercise, the sleep pattern, etc., to information that a user can understand.

A wireless communicator 113 is built into the main body 110. The wireless communicator 113 is mounted onto the circuit board 111 and is thus electrically connected to the processor 112. The wireless communicator 113 may include a Bluetooth® portion, a radio frequency (RF) portion, or the like. The wireless communicator 113 may transmit to a monitoring device, such as a smartphone, the signal that has been processed at the processor 112. Thus, a user can easily monitor his or her biosignals, as well as other relevant information, through the monitoring device.

The main body 110 also includes a display 114. The display 114 is installed in the main body 110 so that a screen is outwardly exposed. The display 114 may present to a user with information in the form of numbers, letters, or the like, derived from the signal processing performed by the processor 112. An operator 115 relays a user's command to the processor 112. Among other things, the operator 115 may include a power button for inputting an on/off command, or in other words, a command for turning on or turning off the power of the wearable device 100.

The battery 180 provides power to the processor 112. The battery 180 is flexible and can be built into the strap 120, or the second strap member 122. Thus, the battery 180 may freely bend along with the second strap member 122. The battery 180 is electrically connected to the processor 112 by an electrical wire 181 that is placed inside the second strap member 122.

The battery 180 may be rechargeable, so that once it depleted it may be recharged. In a case in which the main body 110 is equipped with an input/output (TO) port, such as a universal serial bus (USB) port, the battery 180 may be recharged in such a manner that an external battery is connected to the IO port. The battery 180 may be recharged via a wireless method or solar cells, etc. The battery 180 may be built into the main body 110.

The foregoing exemplary embodiments and advantages are exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A wearable device, comprising:
    a main body;
    a strap connected to the main body, the strap being configured to be flexible;
    a light source disposed in the strap, the light source being configured to emit light onto a surface of a user;
    a spectrum portion disposed in the main body;
    an optical waveguide disposed in the strap, the optical waveguide being configured to receive the emitted light traveling into and out from the surface, and transmit the received light to the spectrum portion; and
    a detector disposed in the main body, the detector being configured to detect the transmitted light dispersing through the spectrum portion.

2. The wearable device of claim 1, wherein the spectrum portion comprises a linear variable filter.

3. The wearable device of claim 1, wherein the spectrum portion comprises:
    a light-transmissive member configured to enable the transmitted light to pass therethrough;
    a reflective mirror disposed on an outer surface of the light-transmissive member, the reflective mirror being configured to reflect the passed-through light; and
    a diffraction grating disposed on the outer surface of the light-transmissive member, the diffraction grating being configured to disperse the reflected light, and transmit the dispersed light to the detector.

4. The wearable device of claim 1, wherein the optical waveguide is an optical fiber.

5. The wearable device of claim 1, further comprising:
    a light-collecting member disposed in the strap, the light-collecting member being configured to collect the emitted light traveling into and out from the surface, and transmit the collected light to the optical waveguide.

6. The wearable device of claim 1, wherein the light source is configured to emit the light having a wavelength of a near-infrared frequency, and
    the detector is configured to detect the dispersed light having the wavelength of the near-infrared frequency.

7. The wearable device of claim 1, wherein the strap comprises:
    a first strap member comprising the optical waveguide therein, the first strap member extending from a first end of the main body;
    a second strap member extending from a second end of the main body; and
    a buckle comprising the light source therein, the buckle being connected to an end of the first strap member, and the buckle being configured to fasten and unfasten the second strap member to and from first strap member.

8. The wearable device of claim 7, wherein the buckle comprises:
    an accommodation groove disposed to face the surface, the accommodation groove being configured to house the light source, and the accommodation groove being inserted a light incident end of the optical waveguide therein; and
    a window configured to enable the emitted light to pass therethrough, and cover the accommodation groove.

9. The wearable device of claim 7, wherein the second strap member comprises a battery therein.

10. The wearable device of claim 1, wherein the strap comprises:
    a first strap member comprising the light source and the optical waveguide therein, the first strap member extending from a first end of the main body; and
    a second strap member extending from a second end of the main body.

11. The wearable device of claim 10, wherein the second strap member comprises a battery therein.

12. The wearable device of claim 1, further comprising:
a processor disposed in the main body, the processor being configured to operate the light source, and process a signal that is received from the detector; and
a battery configured to provide power to the processor.

13. The wearable device of claim 12, further comprising:
an operator configured to relay a command of the user to the processor.

14. The wearable device of claim 12, wherein the battery is configured to be flexible, and
the battery is disposed in the strap.

15. The wearable device of claim 12, further comprising:
a wireless communicator disposed in the main body, the wireless communication being configured to transmit the processed signal.

16. The wearable device of claim 12, further comprising:
a display disposed in the main body, the display being configured to display information of the processed signal.

17. The wearable device of claim 1, wherein the surface of the user is skin of the user.

* * * * *